United States Patent
Plunkett et al.

[11] Patent Number: 5,916,191
[45] Date of Patent: Jun. 29, 1999

[54] PULSATILE FLOW GENERATION IN HEART-LUNG MACHINES

[75] Inventors: Sean D. Plunkett, Mission Viejo; Henry W. Palermo, Burbank, both of Calif.

[73] Assignee: Medtronic, Inc., Minneapolis, Minn.

[21] Appl. No.: 08/643,123

[22] Filed: Apr. 30, 1996

[51] Int. Cl.$^6$ .................................................. A61M 37/00
[52] U.S. Cl. ...................................... 604/4; 422/45
[58] Field of Search .................... 604/4–6, 65; 623/3; 251/4, 5, 61.1; 128/DIG. 3, DIG. 12; 422/44–46

[56] References Cited

U.S. PATENT DOCUMENTS

| | | |
|---|---|---|
| 4,334,180 | 6/1982 | Bramm et al. . |
| 4,492,531 | 1/1985 | Kenji et al. . |
| 4,535,786 | 8/1985 | Kater ............................................ 604/4 |
| 4,610,656 | 9/1986 | Mortensen . |
| 4,976,593 | 12/1990 | Miyamoto . |
| 5,011,469 | 4/1991 | Buckberg et al. ............................ 604/4 |
| 5,186,431 | 2/1993 | Tamari ......................................... 604/4 |
| 5,385,540 | 1/1995 | Abbott et al. ................................ 604/4 |
| 5,588,816 | 12/1996 | Abbott et al. ................................ 604/4 |

*Primary Examiner*—Robert A. Clarke
*Assistant Examiner*—Ki Yong O
*Attorney, Agent, or Firm*—Harry G. Weissenberger

[57] ABSTRACT

Pulsatile blood flow in a heart-lung machine is accomplished by pumping blood into a bladder at a constant rate, and cyclically emptying the bladder into aortic line of the heart-lung machine either by means of the bladder's own elasticity or by a mechanical compression mechanism which can be programmed to simulate the human heartbeat.

3 Claims, 3 Drawing Sheets

PULSATILE FLOW GENERATION IN HEART-LUNG MACHINES

FIELD OF THE INVENTION

This invention relates to heart-lung machines, and more particularly to a method and apparatus for simulating the natural heartbeat's pressure pattern in the blood output of the heart-lung machine.

BACKGROUND OF THE INVENTION

The natural human heart provides the body with a pulsatile flow of blood corresponding to the filling and emptying (beating) of the various chambers of the heart. The instantaneous blood flow rate varies in a complex cyclical manner from near zero to some maximum rate, with the overall blood flow rate being a time weighted average.

The cardiopulmonary bypass circuits of heart-lung machines used in open-heart surgery typically utilize centrifugal or positive displacement (i.e. roller type) pumps to provide the motive power for circulation of the blood. These pumps provide an essentially constant flow rate of blood through the circuit at all times, the instantaneous rate and the average rate being nearly identical.

Medical studies have suggested that pulsatile flow, being more physiologically correct than constant flow, may have a beneficial impact on the efficacy of the extracorporeal perfusion. This can result in improved patient outcomes following cardiac bypass surgery.

Various ways have been proposed to mimic in a heart-lung machine the natural pulsatile flow of the heart, but none of them have so far been satisfactory. The simplest way of providing a pulsed flow is to cyclically clamp and unclamp the inlet or outlet line of the heart-lung machine's arterial pump. Clamping the pump inlet is not desirable since it can create very high suction pressures in the inlet which can damage the red blood cells, or in some cases even cause cavitation which can potentially release gas bubbles into the blood stream. Further, during the low flow or rest periods, the pump rotors spin on a stagnant volume of fluid, which may result in mechanical trauma to the blood cells. Clamping the pump outlet is not desirable in a centrifugal pump due to this mechanical trauma. Clamping the pump outlet is not desirable in a positive displacement pump since the rapid buildup of pressure in the lines can rupture the connections or tubing, potentially resulting in a catastrophic event.

A more acceptable way of creating pulsatile flow is to vary the speed of the pump in a cyclical manner. This is easily accomplished electronically by the pump controller. However, the inertia of the spinning elements of the pump tends to render the resulting waveform more sinusoidal than the natural heartbeat waveform and forces the wave period to be longer than the natural period. In addition, the components of the bypass circuit downstream of the pump, such as the oxygenator and arterial filter, also damp the pulses due to their volumetric holdup.

SUMMARY OF THE INVENTION

The present invention creates a pulsatile flow by causing a continously running pump to fill an elastic bladder with blood through a check valve. The bladder is connected to a blood outlet through an intermittently operable outlet valve. The outlet valve is triggered by the expansion and contraction of the elastic bladder and preferably operates with a hysteresis, i.e. it fully opens when the expansion of the bladder exceeds a predetermined volume, and closes fully when the contraction of the bladder reduces the volume below another, substantially smaller, volume.

In a first embodiment of the invention, a mechanical outlet valve with an appropriate toggle mechanism is directly connected to the bladder so as to snap open when the bladder is fully expanded, and to snap closed when it is nearly empty, the elasticity of the bladder driving the blood through the outlet valve. In a second embodiment, the expansion of the bladder trips a switch or sensor which causes a controller to open the outlet valve and actuate a pressure mechanism which mechanically compresses the bladder to eject the blood. Other known mechanisms with a similar action may also be used.

DESCRIPTION OF THE PREFERRED EMBODIMENTS

Figure 1:
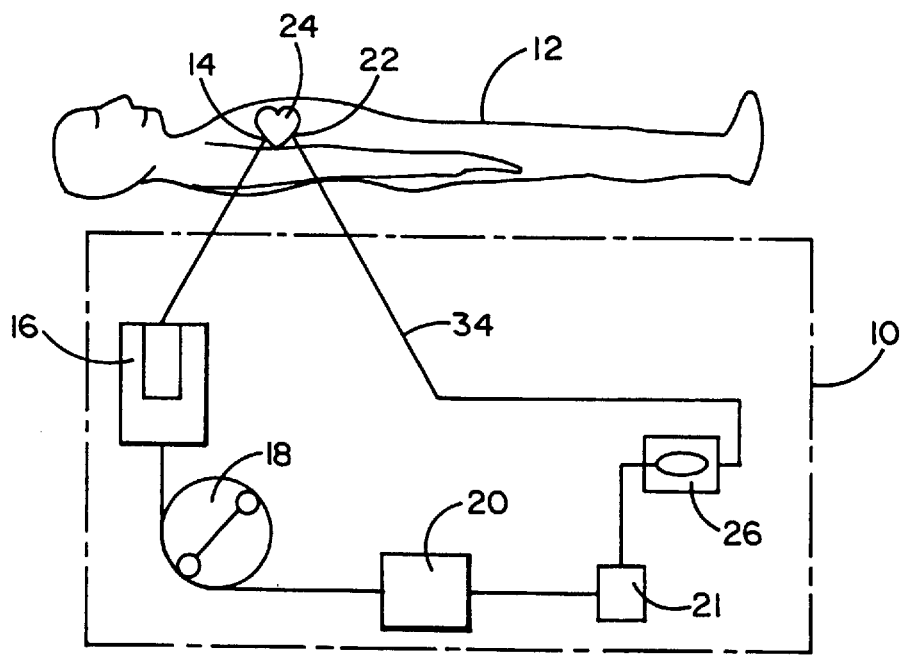
FIG. 1 is a schematic view of a heart lung machine using the invention.

FIG. 1 illustrates in simplified form, the general environment in which the invention is useful. During coronary bypass surgery, a heart-lung machine 10 diverts the blood of patient 12 from the vena cava 14 into a reservoir 16. From there, a pump 18 pumps the blood through an oxygenator 20 and filter 21 back into the aorta 22 of patient 12.

The pump 18 is typically a roller pump running at a substantially steady speed, which is desirable for the proper functioning of the oxygenator 20. The pulsatile action of the natural heart 24 can be simulated, an accordance with the present invention, by interposing between the oxygenator 20 and the aorta 22 a bladder assembly 26 shown in more detail in FIGS. 2a through 4.

Figure 2A:
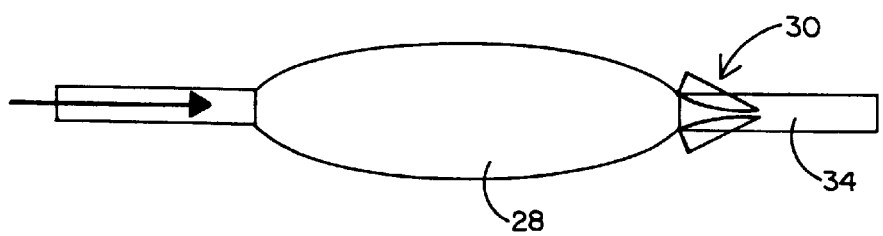
FIG. 2a through 2d are schematic views illustrating four phases in the operation of a first embodiment of the invention.
Figure 2B:
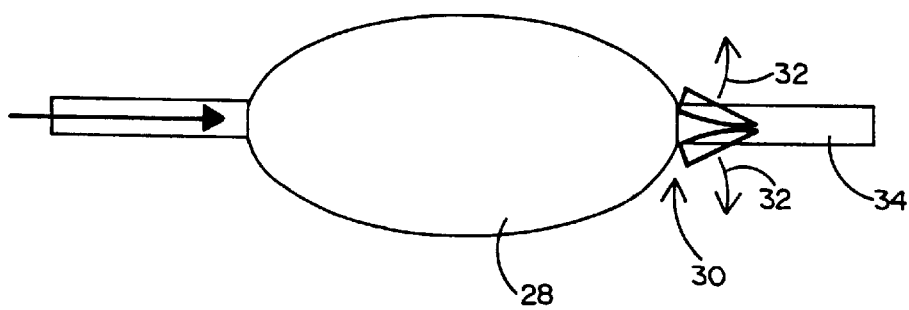
Figure 2C:
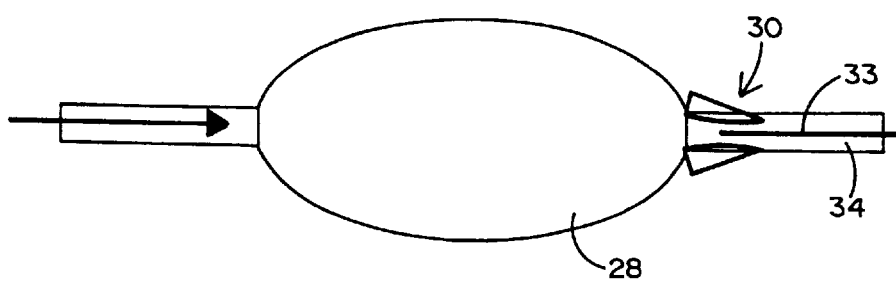
Figure 2D:
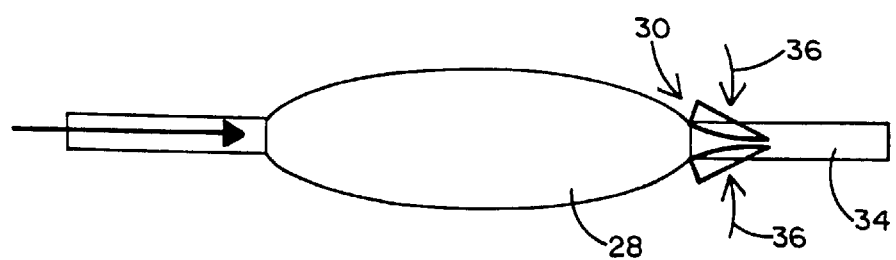

FIGS. 2a through 2d show the operation of a first preferred embodiment of the invention. An elastic bladder 28 receives blood at a steady rate from the oxygenator 20 of FIG. 1. As the blood flows into bladder 28, the bladder 28 expands and pressure builds up in it. When the pressure reaches a predetermined amount, it forces the toggled outlet valve 30 open (arrows 32 in FIG. 2b) allowing the elastic bias of bladder 28 to propel a bolus of blood 33 into the aortic line 34 (FIG. 2c). Due to its toggle action, the outlet valve 30 remains open until the bladder 28 has essentially relaxed. The valve 30 then closes (arrows 36 in FIG. 2d), and the cycle repeats. It will be understood that the flow 33 in aortic line 34 during the phase illustrated in FIG. 2c is considerably greater than the flow being pumped into the bladder 28 by the pump 18.

Figure 3A:
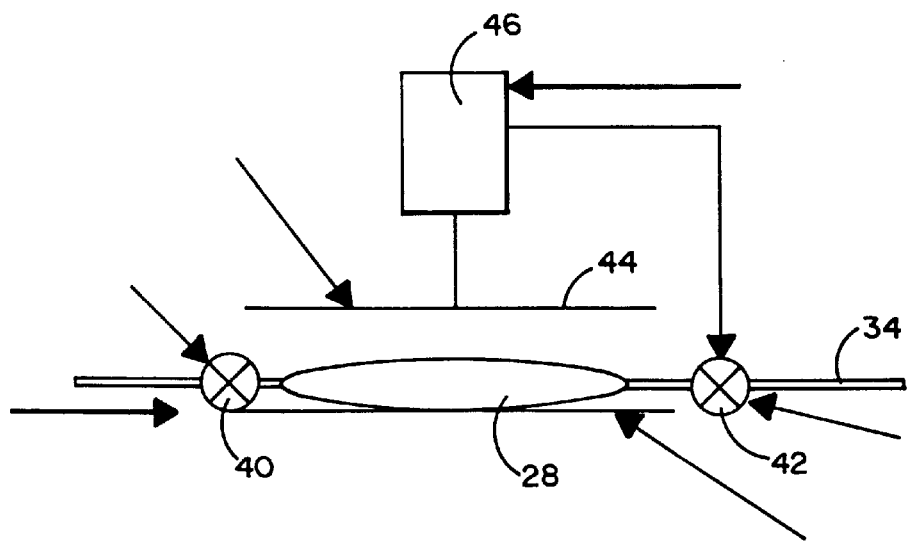
FIG. 3a through 3c are schematic views illustrating similar phases in the operation of a second embodiment of the invention.
Figure 3B:
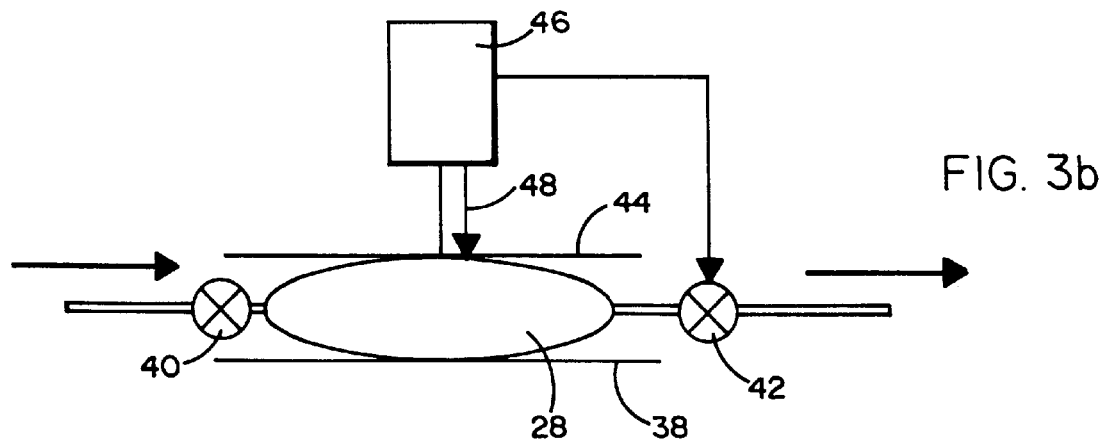
Figure 3C:
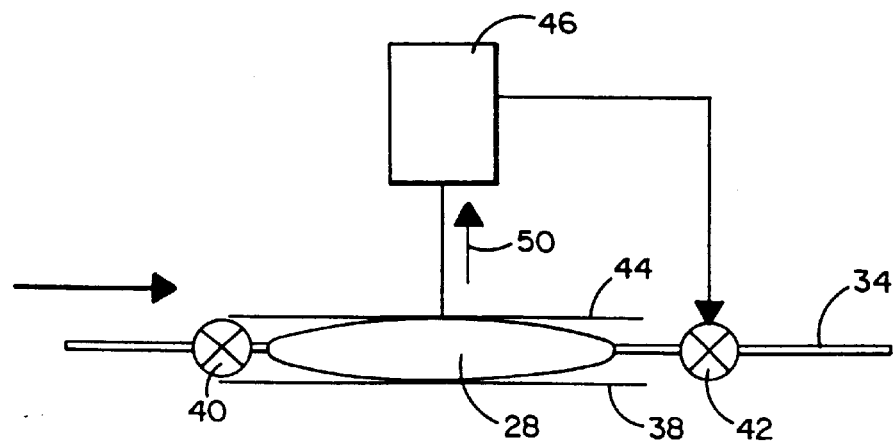

FIGS. 3a–c illustrate a more complex embodiment of the invention. In that embodiment, the bladder 28 is disposed on a fixed plate 38 and receives blood from oxygenator 20 through a check valve 40. A servo-type valve 42 which may be electrically, pneumatically or mechanically controlled normally blocks the aortic line 34.

When the bladder 28 expands from its rest condition of FIG. 3a, it eventually reaches the position of FIG. 3b where it contacts a movable plate 44 which is actuated by a controller 46. In the position of FIG. 3b, an appropriate limit switch or sensor (not shown) activates the controller 46. This causes the controller 46 to open the valve 42 and drive the movable plate 44 downward to squeeze the bladder 28 (arrow 48 in FIG. 3b). After the movable plate 44 travels a predetermined distance downward, the controller 46 shuts the outlet valve 42 and retracts the movable plate 44 to its original position (arrow 50 in FIG. 3c) to repeat the cycle (FIG. 3c).

Figure 4:
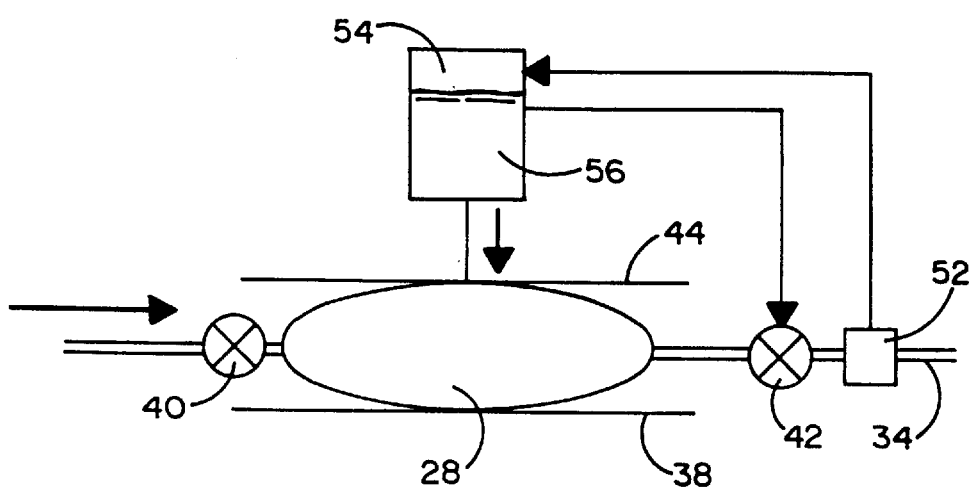
FIG. 4 is a schematic view illustrating an alternative version of the second embodiment.

The advantage of the embodiment of FIGS. 3a–c is that the rate of descent of the movable plate 44 is variable as desired by appropriately programming a microprocessor which controls whatever conventional mechanism drives the plate 44. FIG. 4 illustrates such an arrangement. In FIG. 4, a pressure transducer 52 is provided in the aortic line 34. A signal representative of the blood pressure in the aortic line 34 is applied to the microprocessor 54 which compares the sensed pressure in a feedback loop to a preprogrammed time-amplitude pattern and operates the plate drive 56 to follow the preprogrammed pattern. In this manner, the apparatus of FIG. 4 (unlike the apparatus of FIGS. 2a–d which is less expensive and more reliable but in which the blood output always follows a decreasing exponential curve) can be programmed to simulate the natural heartbeat as closely as the mechanical inertia of the mechanism of plate 44 will allow.

It is understood that the exemplary apparatus for producing pulsatile blood flow in a heart-lung machine described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. Apparatus for producing pulsatile blood flow in a heart-lung machine, comprising:
   a) an extracorporeal blood circuit having an expandable bladder;
   b) a blood intake connected to said bladder
   c) a pump connected to said extracorporeal blood circuit, said pump pumping a supply of blood to said bladder at a substantially constant rate;
   d) a blood outlet for said bladder; and
   e) a pressure-sensitive valve having a hysteresis so as to open said blood outlet when the blood volume in said bladder rises to a first predetermined level, and to close said blood outlet when the blood volume in said bladder drops to a second predeteremined level.

2. The apparatus of claim 1, in which said bladder is elastic, and said elasticity provides the sole bias for ejecting blood into said blood outlet when said valve is open.

3. The apparatus of claim 1, further comprising:
   e) a fixed plate and a movable plate, said bladder being disposed between said plates so as to be squeezable thereby; and
   f) a controller arranged to operate said valve and to move said movable plate to squeeze said bladder while said valve is open;
   g) a microprocessor associated with said controller and arranged to control the squeezing movement of said movable plate in such a manner as to squeeze said bladder in a predetermined pattern;
   h) a pressure sensor in said blood outlet, said pressure sensor being so connected to said microprocessor in a feedback loop as to conform the blood pressure in said blood outlet to a predetermined time-amplitude pattern.

* * * * *